(12) United States Patent
Peter et al.

(10) Patent No.: US 8,529,513 B2
(45) Date of Patent: Sep. 10, 2013

(54) DEVICE FOR METERED ADMINISTRATION OF A LIQUID PRODUCT

(75) Inventors: Daniel Peter, Niederwangen (CH); Simone Gafner-Geiser, Langenthal (CH)

(73) Assignee: Roche Diagnostics International AG, Rotkreuz (CH)

( * ) Notice: Subject to any disclaimer, the term of this patent is extended or adjusted under 35 U.S.C. 154(b) by 725 days.

(21) Appl. No.: 11/388,243

(22) Filed: Mar. 23, 2006

(65) Prior Publication Data

US 2007/0010789 A1 Jan. 11, 2007

(30) Foreign Application Priority Data

Mar. 24, 2005 (EP) .................................... 05006545

(51) Int. Cl.
*A61M 37/00* (2006.01)
(52) U.S. Cl.
USPC ........... 604/155; 604/131; 604/154; 604/207; 604/208; 604/209; 604/210; 604/211; 604/213; 604/214; 604/224
(58) Field of Classification Search
USPC ................. 604/207–211, 213–214, 224, 131, 604/151–155, 218; 310/80
See application file for complete search history.

(56) References Cited

U.S. PATENT DOCUMENTS

| | | | |
|---|---|---|---|
| 4,393,319 A * | 7/1983 | Bock ............................. 310/80 |
| 5,106,375 A | 4/1992 | Conero | |
| 5,492,534 A | 2/1996 | Athayde et al. | |
| 5,582,591 A | 12/1996 | Cheikh | |
| 5,616,123 A | 4/1997 | Cheikh | |
| 6,368,314 B1 * | 4/2002 | Kipfer et al. .................. 604/506 |
| 6,613,023 B2 | 9/2003 | Kirchhofer et al. | |
| 6,620,137 B2 | 9/2003 | Kirchhofer et al. | |
| 7,066,909 B1 * | 6/2006 | Peter et al. ..................... 604/136 |
| 2002/0073782 A1 * | 6/2002 | Chevallet et al. ............... 73/700 |
| 2003/0060767 A1 * | 3/2003 | Peter et al. ..................... 604/151 |
| 2003/0073954 A1 * | 4/2003 | Moberg et al. ................ 604/154 |
| 2004/0122366 A1 | 6/2004 | Kazemzadeh | |

FOREIGN PATENT DOCUMENTS

| | | |
|---|---|---|
| DE | 41 33 402 C1 | 1/1993 |
| DE | 197 17 107 A1 | 11/1998 |
| DE | 198 22 031 A1 | 11/1999 |
| DE | 198 40 992 A1 | 3/2000 |
| DE | 199 00 827 | 8/2000 |
| WO | WO 9847552 A1 * | 10/1998 |
| WO | WO 01/72357 A2 | 10/2001 |
| WO | WO 2004/089448 A1 | 10/2004 |

* cited by examiner

*Primary Examiner* — Bhisma Mehta
*Assistant Examiner* — Larry R Wilson
(74) *Attorney, Agent, or Firm* — Dinsmore & Shohl LLP

(57) ABSTRACT

A device for administering an injectable substance, the device including a housing, a translation member moveable in a translation direction, a rotation member rotatably moveable about a rotation axis and coupled to the translation member to support the translation member counter to the translation direction, a rotary bearing including a bearing body bearing the rotation member rotatably about the rotation axis, the rotary bearing having support surfaces for supporting the rotation member axially on the bearing body, and a device for reducing play whereby at least two support surfaces are brought into contact with a pressing force, thereby reducing an axial play of the rotary bearing.

43 Claims, 7 Drawing Sheets

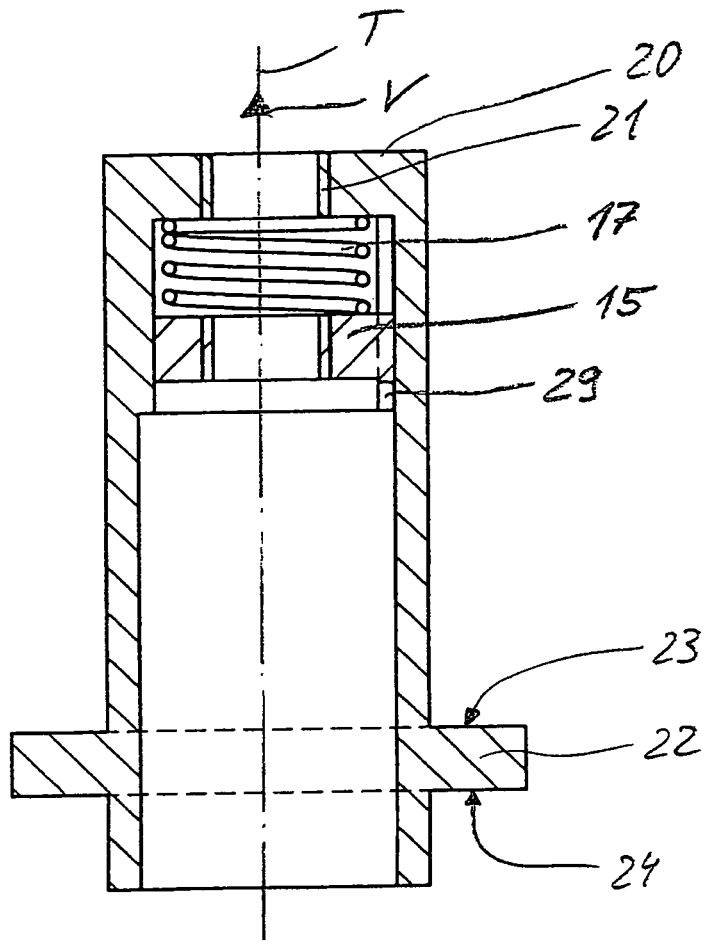
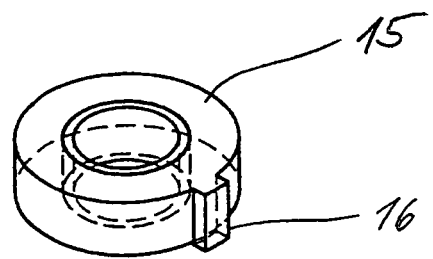

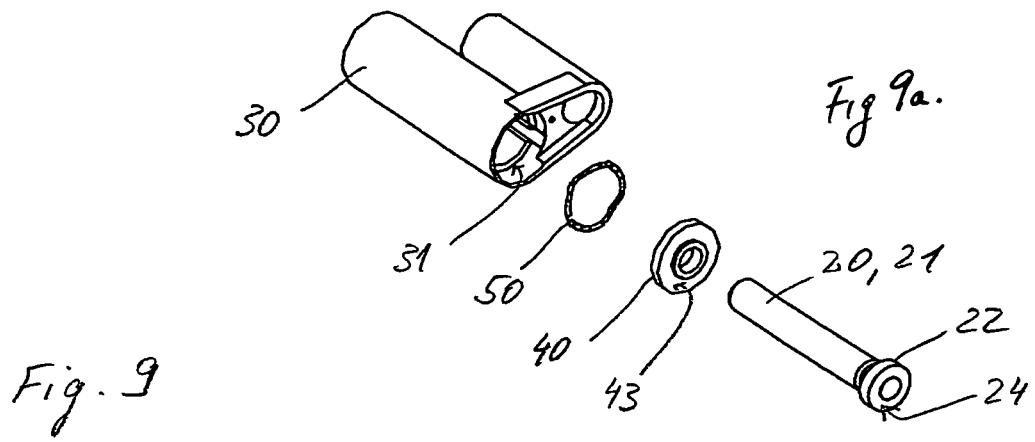
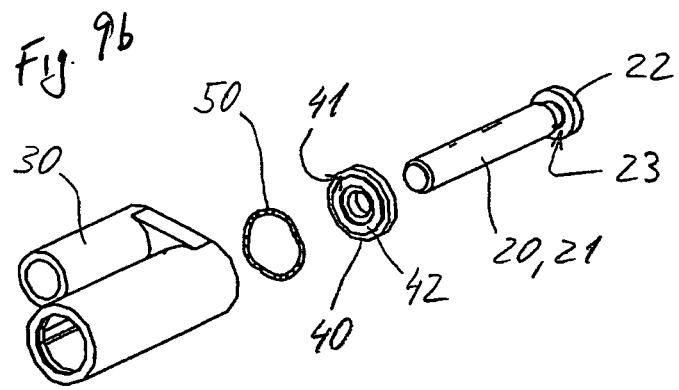
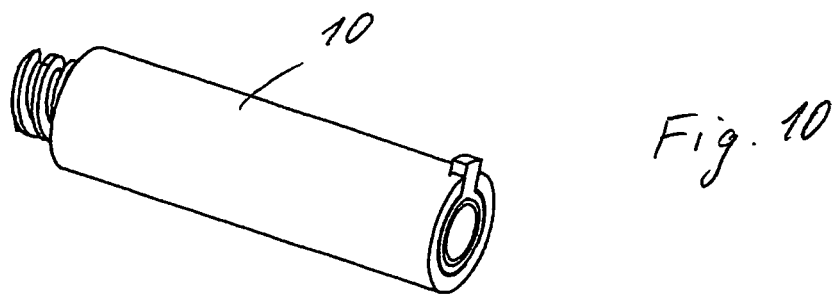

DEVICE FOR METERED ADMINISTRATION OF A LIQUID PRODUCT

CROSS-REFERENCE TO RELATED APPLICATION

This application claims the benefit of German Application No. 05006545.7, filed on Mar. 24, 2005, the contents of which are incorporated in its entirety by reference herein.

BACKGROUND

The present invention relates to devices and methods for delivering, administering or dispensing substances, and to methods of making and using such devices. More particularly, it relates to devices and methods for metered administration of liquid products in biotechnology applications, preferably in medical applications, including veterinary and pharmaceutical applications. It relates in particular to infusion and injection appliances and devices, and methods of making and using such appliances and devices.

In various treatments, great importance is attached to the accuracy of the metering of products to be administered, for example in the administration of insulin in the treatment of diabetes. Infusion appliances and injection appliances are common in which a product to be administered is dispensed from a product reservoir by means of a motor-driven reciprocating piston pump in the case of infusion appliances or by means of a manually activated reciprocating piston pump in the case of injection appliances. In infusion appliances, the reciprocating piston is usually driven by a rotary drive mechanism, the rotation movement of the drive mechanism being converted by means of a spindle drive into the linear movement of the piston. In injection appliances, a spindle drive is often used for selecting the product dose to be administered, while the linear movement of the piston is effected directly by hand. In injection appliances, rack-and-pinion gears are also customary. A common feature of the above examples of appliances used for administration is that the accuracy of the metering depends critically on the degree of precision with which it is possible to predetermine the distance that the piston has to travel to deliver a defined dose of product.

Infusion appliances and injection appliances of the type mentioned above are described by DE 198 40 992 A, DE 198 22 031 C and DE 199 00 827 C, for example.

Particular demands on metering accuracy and precision have to be met by infusion appliances with which the product is often dispensed, delivered or administered over fairly long periods of time in small and discrete boluses or doses. Structural features serving in principle to improve the accuracy of the metering may at the same time also have a disruptive effect on, for example, the capacity for occlusion detection. An infusion appliance with advantageously configured, automatic occlusion detection is described in DE 198 40 992, to which reference is hereby made for the purposes of the present invention. A further appliance with occlusion detection is described in WO 01/72357 A2. For the occlusion detection, the entire delivery means is supported on the housing of the infusion appliance via a sensor. To ensure that this manner of support does not permit relative movements between the delivery means and the product container, WO 01/72357 A2 proposes, for assembly of the appliance, that the entire delivery means is first pressed in the delivery direction of the piston as far as an abutment formed by the housing, that the delivery means is then essentially relieved of the pressure, and finally that a closure cap is fitted into a rear opening of the housing and is adhesively bonded to the housing. The cap is intended to hold the delivery means in abutment against the housing. As an alternative configuration, it is also proposed that the delivery means, at its end remote from the piston, is supported on the rear base of the housing by means of an elastic sealing ring, and that a hollow space remaining between the rear face of the delivery means and the base of the housing is filled with a filler material, for example with silicone. The filler material should be substantially non-compressible, so as not to relieve the load on the sensor.

SUMMARY

It is an object of the invention to deliver a desired dose of product more accurately than before possible with devices for metered administration of liquid products.

In one embodiment, the present inventon comprises a device for administering an injectable substance comprising a housing, a translation member moveable in a translation movement, a rotation member rotatably moveable about a rotation axis and coupled to the translation member to support the translation member counter to the translation movement, a rotary bearing including a bearing body bearing the rotation member rotatably about the rotation axis, the rotary bearing having support surfaces for supporting the rotation member axially on the bearing body, and a device for reducing play whereby at least two support surfaces are brought into contact with a pressing force, thereby reducing an axial play of the rotary bearing. In one embodiment, one of the translation and rotation movements produces the other, and in one embodiment, the support surfaces comprise a first, second, third and fourth support surface, the first support surface and the second support surface being connected axially rigidly to the bearing body and either facing away from one another axially or facing towards one another axially, and the third support surface facing axially towards the first support surface and the fourth support surface facing axially towards the second support surface and being axially rigidly connected to the rotation member.

A device for metered administration of a liquid product, in accordance with the present invention, comprises a housing, a reservoir for the product, and a delivery means. The housing itself can form the reservoir directly. In some preferred embodiments, however, a container, for example an ampoule or the like, forms the reservoir. For such a container, the housing forms a receiving seat for holding the container in a defined position. Such a container may preferably be inserted into the housing. As is already customary in the case of ampoules, the container can be prefabricated by being filled with a defined quantity of product and sealed by a piston in the container that seals the rear of the container. Prefabricated ampoules of this kind are customary for self-administration of insulin in the treatment of diabetes. The product can be the aforementioned insulin, a growth hormone, and, in principle, any other medically active or, for example, cosmetically active product. In some embodiments, the device according to the present invention is preferably designed for self-administration.

The delivery means or mechanism comprises at least one rotation member and at least one translation member. For delivery of the product, the at least one rotation member executes a rotation movement relative to the housing and about a rotation axis. For delivery of the product, the at least one translation member executes a translation movement relative to the reservoir and, at least during the execution of the translation movement, is mechanically coupled to the rotation member in such a way that the rotation movement produces the translation movement or the translation movement produces the rotation movement. At least during the execution of the translation movement, the rotation member and the translation member are also mechanically coupled to one another in such a way that the rotation member supports the translation member counter to or against the direction of the translation movement, which, however, is intended to include the case where the rotation member and the translation member jointly execute a translation movement. The translation movement of the translation member can be superposed by a rotation movement, although, in some embodiments, the translation member preferably executes only the translation movement. The translation movement may preferably be a linear movement.

In some preferred embodiments, the rotation member is preferably driven by a motor if the administering device is an infusion appliance or device. In some preferred embodiments, if the administering device is an injection device, the dose of product to be administered may preferably be selected with the rotation member, the rotation movement for selection being effected by hand.

In embodiments of the present invention, the term "axial" designates the rotation axis of the rotation member. Preferably, the rotation axis not only has the translation direction as a direction component, but points in the translation direction and, in the case of an axial linear movement of the translation member, is substantially identical to the translation axis of this movement.

The device moreover comprises a rotary bearing for the rotation member. The rotary bearing comprises a one-part or multi-part bearing body which bears the rotation member rotatably about the rotation axis and on which the rotation member is axially supported. The bearing body can be formed by the housing, or it is a body which is separate from the housing and which is supported axially on the housing. In the case of a separate bearing body, the housing, in simple configurations, should support the bearing body such that it cannot move axially relative to the housing. In similarly preferred embodiments, however, the bearing body is axially movable relative to the housing. In such embodiments, the housing supports the bearing body, and with it the delivery means, in a manner permitting axial floating. In the case of a bearing body that is axially movable relative to the housing, measures should be taken which reduce an axial play between the bearing body and the housing or, in some preferred embodiments, which do not allow such axial play to exist in the first place.

The rotary bearing of the rotation member has at least four support surfaces in order to support the rotation member axially on the bearing body. A first and a second of the support surfaces are connected axially rigidly to the bearing body. A third and a fourth of the support surfaces are connected axially rigidly to the rotation member. Of these support surfaces, either the support surfaces connected axially rigidly to the bearing body or the support surfaces connected axially rigidly to the rotation body face axially away from one another, and the respective other support surfaces face axially towards one another. In some embodiments, the support surfaces connected axially rigidly to the bearing body preferably face axially towards one another. Moreover, the first support surface and the third support surface face axially towards one another, and the second support surface and the fourth support surface face axially towards one another. Facing axially towards one another signifies those pairs of support surfaces whose surface normals point in axially opposite directions to one another. The surfaces of the respective surface pair do not have to be axially aligned. Nor do they have to lie directly opposite one another. The statement that a support surface is connected axially rigidly to the bearing body or the rotation member is intended to signify that the respective support surface is formed either directly by the bearing body or the rotation member, i.e., in one piece, or that a further body forms the support surface in question and that this further body is connected to either the bearing body or the rotation member in an axially immovable manner, preferably completely rigidly. Where axial forces arise between the rotation member and the bearing body, these axial forces are transmitted via said support surfaces from the rotation member to the bearing body or from the bearing body to the rotation member. In this sense, the rotation member is axially supported on the bearing body via the support surfaces.

According to the present invention, the rotary bearing comprises a device for reducing play. With the device for reducing play, at least two of the support surfaces facing axially towards one another are clamped axially to one another with a pressing force, such that an axial play of the rotary bearing is eliminated or at least reduced. Although the axial pressing force should, on the one hand, be sufficient to eliminate or at least reduce the axial play of the rotary bearing, the pressing force should, on the other hand, nevertheless be as small as possible, since it contributes to an increase in the bearing friction. The two other support surfaces which face axially towards one another are either moved axially away from one another by the pressing force or are likewise clamped to one another. This depends on the location at which the pressing force is introduced into the rotary bearing. Thus, the pressing force between two support surfaces that axially face towards one another can act by moving the two support surfaces away from one another and clamping the other two support surfaces to one another. The pressing force can also be applied from outside and, in this case, both pairs of support surfaces facing axially towards one another are axially clamped to one another.

In a preferred embodiment, the device for reducing play generates the pressing force as elasticity force. Although the elasticity force can be generated pneumatically, for example, in some preferred embodiments, the device for reducing play comprises a mechanical spring that generates the pressing force. The elasticity of the spring can be based on material elasticity, for example by using an elastomer spring. However, in some preferred embodiments, the elasticity is preferably an elasticity of shape. The spring can, for example, be a compressed helical spring. However, in some preferred embodiments, the spring acts in the manner of a leaf spring, in order to save axial length. The spring can be formed as an axially elastic annular body that surrounds the rotation member. If, as is preferred, the spring is formed as a leaf spring or acts in the manner of a leaf spring, such an annular body can be undulated about its perimeter, such that the elasticity force is generated by an axial compression of the undulated shape of the annular body. The spring may preferably be installed with an axial pretensioning force. The axial pretensioning force should be as slight as possible in order to keep the bearing friction to a minimum. It should, however, be greater than an axial force that may in practice act on the delivery means in the event of what is called a siphoning effect. Siphoning may occur when product runs out of the reservoir on account of its own weight, i.e., on account of gravity, and the delivery means is sucked along with the escaping product. However, siphoning can be prevented by installing an overpressure valve at or downstream from an outlet of the reservoir. Moreover, the spring force is intended to prevent a situation where, under the expected conditions of use, the translation member is able to lift, together with the rotation member, from a support surface of the bearing body against which the rotation member is clamped by the spring. The spring force should compensate at least for the own weight of translation member and rotation member. In devices that do not have said overpressure valve, it should also compensate for the suction force caused by a siphoning effect.

The pressing force can act on the rotation member in the translation direction of the translation member, if in fact the rotation member, in the direction of translation, is in abutment against one of the support surfaces of the bearing body. However, the pressing force can instead also act on the rotation member counter to the translation direction and force the rotation member, counter to the translation direction, into abutment against one of the support surfaces of the bearing body. The abutment contact can be formed directly between one of the support surfaces of the rotation member and one of the support surfaces of the bearing body, or indirectly via one or more intermediate bodies. Such an intermediate body can be formed by a roller bearing or other suitable structure or mechanism. In a preferred embodiment, the two relevant support surfaces of the rotary bearing are directly in abutment contact with one another, i.e., they form a slide rotary bearing with one another.

In a preferred further embodiment, or also in a development of the embodiment with a spring, the device for reducing play forms at least one of said support surfaces, preferably exactly one of said support surfaces. If the device for reducing play forms one of the support surfaces connected axially rigidly to the bearing body, the device for reducing play is in an adjustment engagement with the bearing body. In this case, the device for reducing play can be displaced relative to the bearing body along a displacement path defined by the adjustment engagement and is displaced into an adjustment position and axially secured relative to the bearing body in the adjustment position such that an axial play of the rotary bearing is reduced or eliminated. In the adjustment engagement with the bearing body, the first support surface and the second support surface are thus axially displaced relative to one another and are axially secured relative to one another in the adjustment position. If the device for reducing play forms one of the support surfaces connected axially rigidly to the rotation member, it is in a corresponding adjustment engagement with the rotation member in which the third support surface and the fourth support surface are displaced relative to one another into an adjustment position and are axially secured relative to one another in the adjustment position such that the axial play of the rotary bearing is reduced and preferably eliminated. The length of displacement available in the adjustment engagement should be such that the adjustment position is not defined by abutment of the device for reducing play against the body with which it is in the adjustment engagement.

The rotary bearing can comprise a roller bearing. Conventional roller bearings have an inherent axial play. The roller bearing of the device according to the invention is also produced for a specific fit and thus associated with tolerances. According to the invention, however, in preferred embodiments with roller bearings, one of the support surfaces can be axially displaced relative to the others and, in this way, the inherent axial play resulting from the unavoidable tolerances can be reduced. One of the support surfaces that is axially rigidly connected to the bearing body supports the roller bearing in an axial direction. A support surface which axially faces towards this support surface, and which is connected axially rigidly to the rotation member, supports the roller bearing in the other axial direction. The roller bearing has, in relation to the rotation axis of the rotation member, a radially outer bearing ring and a radially inner bearing ring. Advantageously, the roller bearing is axially supported on the rotation member only with one of the rings and is axially supported on the bearing body only with the other of the rings. The rotary bearing can comprise a further roller bearing which is arranged in the same way between the two remaining support surfaces of the rotary bearing and is axially supported by these support surfaces. The further roller bearing also has a radially inner bearing ring and a radially outer bearing ring in relation to the rotation axis. In some embodiments, in the further roller bearing, too, only one of the bearing rings is supported axially on the rotation member and only the other of the bearing rings is supported axially on the bearing body. The support surfaces that are connected axially rigidly to the bearing body should lie in a first axial alignment and/or the support surfaces that are axially rigidly connected to the rotation member should lie in a second axial alignment. If the rotary bearing has two roller bearings, in these embodiments either the inner bearing rings or, preferably, the outer bearing rings of both roller bearings are supported axially on the support surfaces facing towards the bearing body and, accordingly, either the outer bearing rings or the inner bearing rings of both roller bearings are supported axially on the support surfaces facing towards the rotation member.

The rotary bearing can also be purely a slide bearing. In such an embodiment, the support surfaces of the rotation member and of the bearing body that face towards one another in respective pairs slide directly on one another when the rotation member executes its rotation movement relative to the bearing body. Finally, the rotary bearing can also be a combination of a slide bearing and a roller bearing.

In a preferred embodiment of the present invention, the adjustment engagement of the device for reducing play with either the rotation member or preferably the bearing body is obtained with a form fit and force fit. The adjustment engagement is preferably continuous in the sense that the axial play can be decreased continuously in the adjustment engagement. The adjustment engagement is preferably self-locking over the length of the displacement path. A preferred example of a continuous adjustment engagement is a threaded engagement between the device for reducing play and preferably the bearing body or between the device for reducing play and the rotation member.

The threaded engagement also provides the advantage that the device for reducing play is axially supported by the adjustment engagement itself in each position it assumes along the entire displacement path available in the adjustment engagement, and it is therefore connected axially rigidly to the body with which it is in the adjustment engagement.

In the case of the threaded engagement, the device for reducing play can be secured in the adjustment position simply by self-locking. However, in some embodiments, the device for reducing play is preferably fixed cohesively in its adjustment position, even when the adjustment engagement is, as preferred, a threaded engagement.

In some embodiments, the displaceable device for reducing play is preferably formed in one piece as a single adjustment member which in the adjustment engagement is axially rigid at least to the extent corresponding to the axial play that is to be reduced. In the case of a multi-part device for reducing play, such a device for reducing play should be inherently axially rigid at least when it is secured in the adjustment position. Thus, for example, a two-part device for reducing play could have a first adjustment member which is in adjustment engagement with the bearing body, and a second adjustment member which is in adjustment engagement with the rotation member. The two adjustment members would be displaced axially relative to one another into the adjustment position and, in the adjustment position, would have to be secured axially on one another or secure themselves automatically on one another in order to obtain the axial rigidity.

In some preferred embodiments, the rotation member preferably drives the translation member. In the translation movement, the translation member can act directly on the product located in the reservoir, for example by itself forming a reciprocating piston or being permanently connected to a reciprocating piston. However, it can also simply press in a loose state against a reciprocating piston. A configuration is also possible in which the translation member acts only via a transmission member or several transmission members on a delivery element, for example a reciprocating piston, which acts directly on the product when it executes the translation movement. The rotation member can form the initial stage of a telescoping delivery means, as is described in DE 197 17 107 A, to which, in this respect, reference is hereby made. In principle, however, the translation member could also drive the rotation member, particularly when the rotation member acts on the product only via one or more transmission members.

In some embodiments, the coupling between the rotation member and the translation member is preferably a flank engagement which is formed by the rotation member and the translation member each having at least one engagement flank. In some preferred embodiments, the at least one engagement flank of the rotation member is formed directly on the rotation member, and the at least one engagement flank of the translation member is formed directly on the translation member.

For production reasons, flank engagements, such as are known in particular from threaded engagements, but also from other cam guides, have an axial play transverse to the engagement flanks, and this axial play may impair the metering accuracy. An axial play may become particularly noticeable if what is called a siphoning effect occurs, i.e., if a suction situation arises in the container as a result of the flow conditions.

In some preferred embodiments, therefore, a further device for reducing play can be provided which is in an adjustment engagement, both with the rotation member and also with the translation member, in which the further device for reducing play is displaced relative to the rotation member and the translation member into an adjustment position and is secured in the adjustment position such that the axial play inherent to the flank engagement is reduced, compared to the known couplings, or is preferably completely eliminated. The adjustment engagement with one of the two members, namely rotation member and translation member, corresponds to the flank engagement between the rotation member and the translation member. The other adjustment engagement defines the displacement movement of the play-reducing device along its displacement path.

In some embodiments, the adjustment engagement with the rotation member is preferably obtained with a form fit and force fit, and it may be preferably a threaded engagement. The same preferably applies as regards the adjustment engagement with the translation member. Forming both the adjustment engagements of the further device for reducing play as threaded engagements is especially expedient when the flank engagement between the rotation member and the translation member is also a threaded engagement, as is preferred in some embodiments of the present invention. However, it is also possible, for example, for the adjustment engagement that defines the displacement movement to be configured as the engagement of an engagement member of the play-reducing device in a guide track purely with a form fit and, by means of an elasticity force, to form the other of the two adjustment engagements with a form fit and force fit. In some preferred embodiments, the adjustment engagement of the further play-reducing device defining the displacement movement is continuous in the sense that the axial play between the rotation member and the translation member can, in this adjustment engagement, be decreased continuously from its production-related initial value to preferably a value of zero, as is permitted, for example, by a preferred threaded engagement. If the delivery means has a telescoping design, a further device for reducing play is in each case advantageously provided between each pair of telescope stages situated in flank engagements.

In some preferred embodiments, the further device for reducing play is secured on one of the members, namely rotation member and translation member, against axial movements relative to the member in question. The securing can be obtained by the further device for reducing play moving along with the rotation movement when the securing is between the rotation member and the device for reducing play, and moving along with the translation movement when the securing is between the further device for reducing play and the translation member.

In the illustrative case of threaded engagement, the further device for reducing play can be secured in one of the adjustment engagements in the adjustment position simply by self-locking. However, in some embodiments, the further device for reducing play is preferably secured cohesively in its adjustment position, even when the secured adjustment engagement is a threaded engagement. The cohesive securing preferably takes place in the adjustment engagement with the rotation member. However, securing on the translation member would in principle also be possible with reversed kinematics. Instead of the securing being done only in one of the two adjustment engagements, the securing can also be done by the further device for reducing play cooperating with the drive member and the output member, in this case by the further device for reducing play being elastically supported both on the drive member and also on the output member.

BRIEF DESCRIPTION OF THE DRAWINGS

FIG. 4 depicts a device for reducing play in an alternative configuration, FIG. 5 shows an adjustment member of the device for reducing play from FIG. 4, FIGS. 9a and 9b, shows components of the administering device in the illustrative embodiment of FIG. 6 in an exploded view, and FIG. 10 shows the translation member of the illustrative embodiment of FIG. 6.

DETAILED DESCRIPTION

Figure 1:
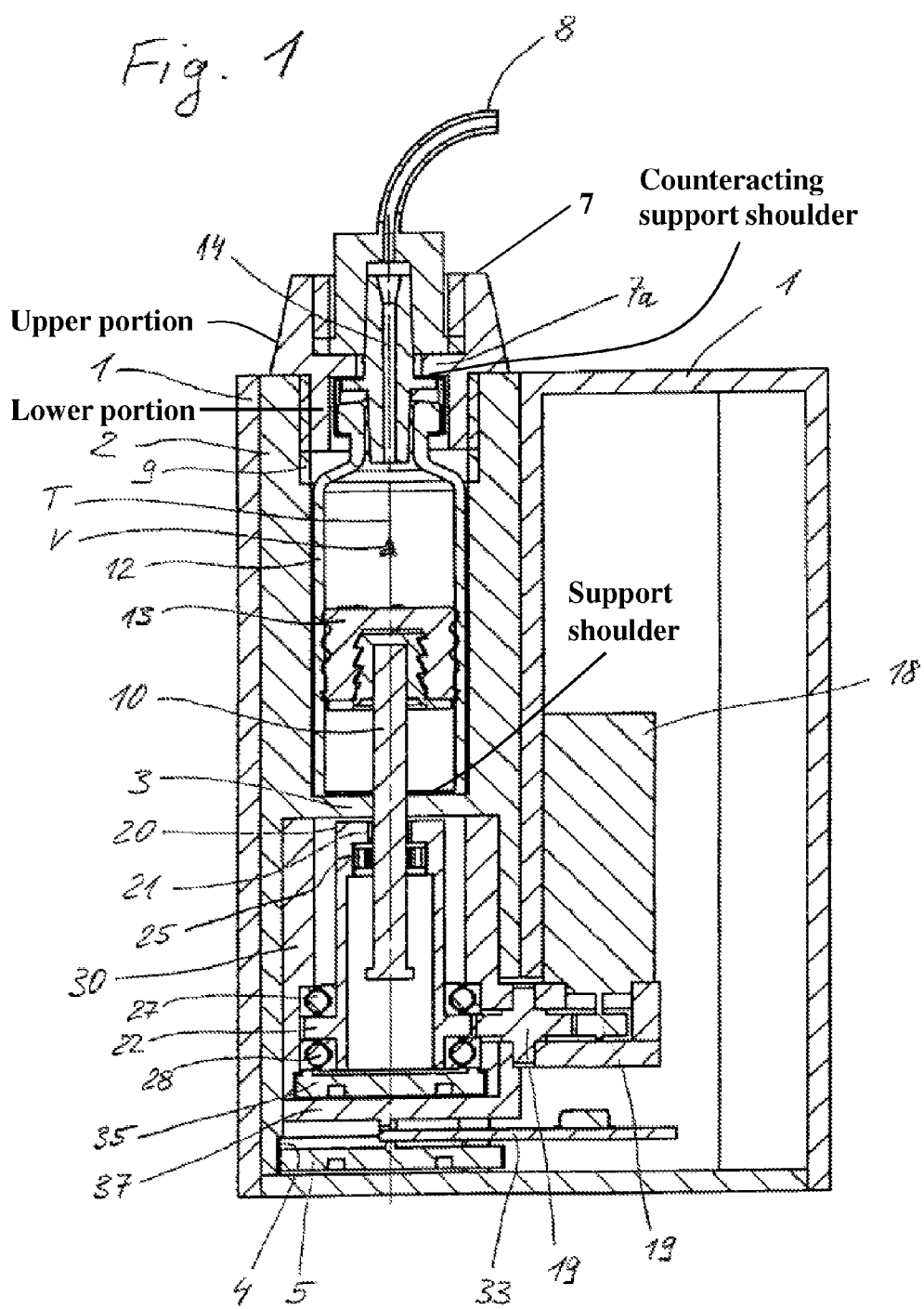
FIG. 1 is a longitudinal section through an administering device in one illustrative embodiment of the present invention.

An infusion appliance, representing an example of an administering device, is shown in longitudinal section in FIG.

1. The appliance has a housing with a first housing structure 1, and with a second housing structure 2, a container 12 filled with an injectable product, and a delivery means or mechanism which functions to deliver or force the product in metered amounts from the container 12 and through an adjoining catheter 8 in order to administer it. The administration can take place subcutaneously in particular, as is customary in the treatment of diabetes, for example. The first housing structure 1 surrounds the second housing structure 2 and is designated below as the shell structure 1. The second housing structure 2 supports components of the infusion appliance and is designated below as the support structure 2.

At one end, which may be referred to as the front end, the container 12 has a longitudinal axis and an outlet 14 via which the interior of the container is connected to the catheter 8, which is coaxial with the longitudinal axis of the container 12. In the container 12, a piston 13 is received in such a way that it can move along a translation axis T in a delivery direction V towards the container outlet 14. The container 12 is open at its rear end. However, the piston 13 seals the container 12 off at the rear end.

The shell structure 1 forms a fixed shell in which the support structure 2, which is formed in one piece by a support body 2, is inserted and secured and forms a chassis of the housing. The shell structure 1 and the support body 2 substantially form the housing of the device. The support body 2 forms a first receiving space in which the container 12 is fitted, and a second receiving space for the delivery means. The container 12 rests with its rear free edge abutting against a radially inwardly projecting support web 3 of the support body 2 forming a support shoulder. The first receiving space formed by the support body 2 has, at the front end, an opening through which the container 12 is inserted. After insertion of the container 12, the opening is closed with a lid 7. The lid 7 is screwed onto the support body 2, which is provided with a thread 9 for this purpose. The support body 2 and the lid 7 could, however, each be provided with another engaging means for releasable engagement, for example with cooperating catches. The lid 7 also forms the connection element between the catheter 8 and the outlet 14 of the container 12. The lid 7 has, for the support shoulder of the support web 3, a counteracting support shoulder on a counteracting support web 7a which presses against a front edge of the container 12 and thus presses the container 12 in abutment against the support web 3 so that the container 12 is axially fixed relative to the support body 2. The lid 7 thus forms a front closure element 7a, and the support web 3 forms a rear closure element 3 of the first receiving space. The first receiving space is further shaped in such a way that the container 12 has the correct position and orientation in relation to the translation axis T. As a result, the support body 2 supports the container 12 axially in and counter to the delivery direction V with a form fit, i.e. by contact with the webs 3 and 7a serving as abutments. In a comparable way, the delivery means is supported axially between other abutments of the support body 2.

Still referring to FIG. 1, the housing has a perimeter and longitudinal axis. The product reservoir has a width and a longitudinal axis. The lid 7 has a counteracting support web 7a to axially fix the container 12 for the injectable product against a support shoulder, the container 12 for the injectable product has a top and the top has a width, the lid 7 comprises a lower portion substantially providing threaded engagement with the support body 2 of the housing via support body 2 threads 9 with engagement being along the longitudinal of the product reservoir, and an upper portion providing the support web 7a that when fully engaged extends beyond the perimeter of the housing, touching an external portion of the perimeter of the housing and extending substantially perpendicular to the longitudinal axis of the product reservoir along the perimeter of the housing and extending beyond the width of the product reservoir, such that when the lid 7 is fully engaged the counteracting support web 7a abuts the top of the container 12 for the injectable product and is oriented perpendicular to the longitudinal axis of the housing 2, extending inwardly so as to form an opening of a smaller width than the width of the top of the container filled with injectable product. The outlet 14 of the container 12 also extends through the counteracting support web 7a and into the catheter 8.

The delivery means comprises the piston 13, an output member 10, a drive member 20 and a motorized rotary drive. The output member 10 forms a translation member of the delivery means, and the drive member 20 forms a rotation member of the delivery means.

The output member 10 is a piston rod, e.g., a piston rod provided with a thread. In the illustrative embodiment, the output member 10 is provided with an outer thread 11 which can be seen in the longitudinal section in FIG. 2. The output member 10 extends through the support web 3 so that it protrudes into the first receiving space and the second receiving space of the support body 2. At its front end, the output member 10 is screwed onto the piston 13. The screw connection is established upon insertion of the container. The support web 3 guides the output member 10 linearly along the translation axis T. The support web 3 secures the output member 10 against twisting relative to the support body 2. In the illustrative embodiment, the thread 11 is for this purpose interrupted by at least one axial groove or flat in which the support web 3 engages.

The drive member 20 is arranged within the second receiving space of the support body 2. It is rotationally symmetrical with respect to the translation axis T. It is sleeve-shaped and can therefore also be designated as drive sleeve. At a front end of the sleeve, the drive member 20 forms a radially inwardly projecting web through which the output member 10 extends. On the inwardly projecting web, the drive member 20 forms an inner thread 21 which is in a threaded engagement with the outer thread 11 of the output member 10.

The drive member 20 is mounted such that it is rotatable about the translation axis T, but not axially movable relative to the support body 2. In a rear area, it has a radially outwardly projecting circumferential web 22 which is provided with an outer toothing. The drive member 20 is moved in rotation about the translation axis T via the outer toothing. Its rotary drive derives from a torque motor 18 which is accommodated in a further receiving space. The further receiving space is formed by the shell structure 1 and is separated from the two receiving spaces of the support body 2. The motor 18 drives the drive member 20 via a toothed gearing with radial teeth 19, of which an output toothed wheel 19 meshes with the outer toothing of the drive member 20. The threaded engagement between the drive member 20 and the output member 10 and the linear guiding of the output member 10 means that, when the drive member 20 is moved in rotation, its rotary drive movement results in an axial output movement of the output member 10 in the delivery direction V. The product displaced by the piston movement is dispensed through the catheter 8 and in this way administered.

Like any threaded engagement, the threaded engagement as such between the output member 10 and the drive member 20 is also associated with an axial play. The metering accuracy of the dispensing operation is therefore associated with a degree of imprecision, at least to the extent of this inherent axial play. For example, in the event of suctioning of the piston 13 on account of siphoning, or in the event of mechanical jolts or pressure differences between the housing interior and the environment, it can happen that the flanks of the outer thread 11 of the output member 10 lift from the driving thread flanks of the thread 21. The exact axial position of the piston 13 is therefore uncertain, to the extent of the axial play of the threads 11 and 21.

However, in accordance with the present invention, a device for reducing the play is provided which is formed by an adjustment member 25 and which virtually or substantially eliminates the axial play between the output member 10 and the drive member 20.

Figure 2:
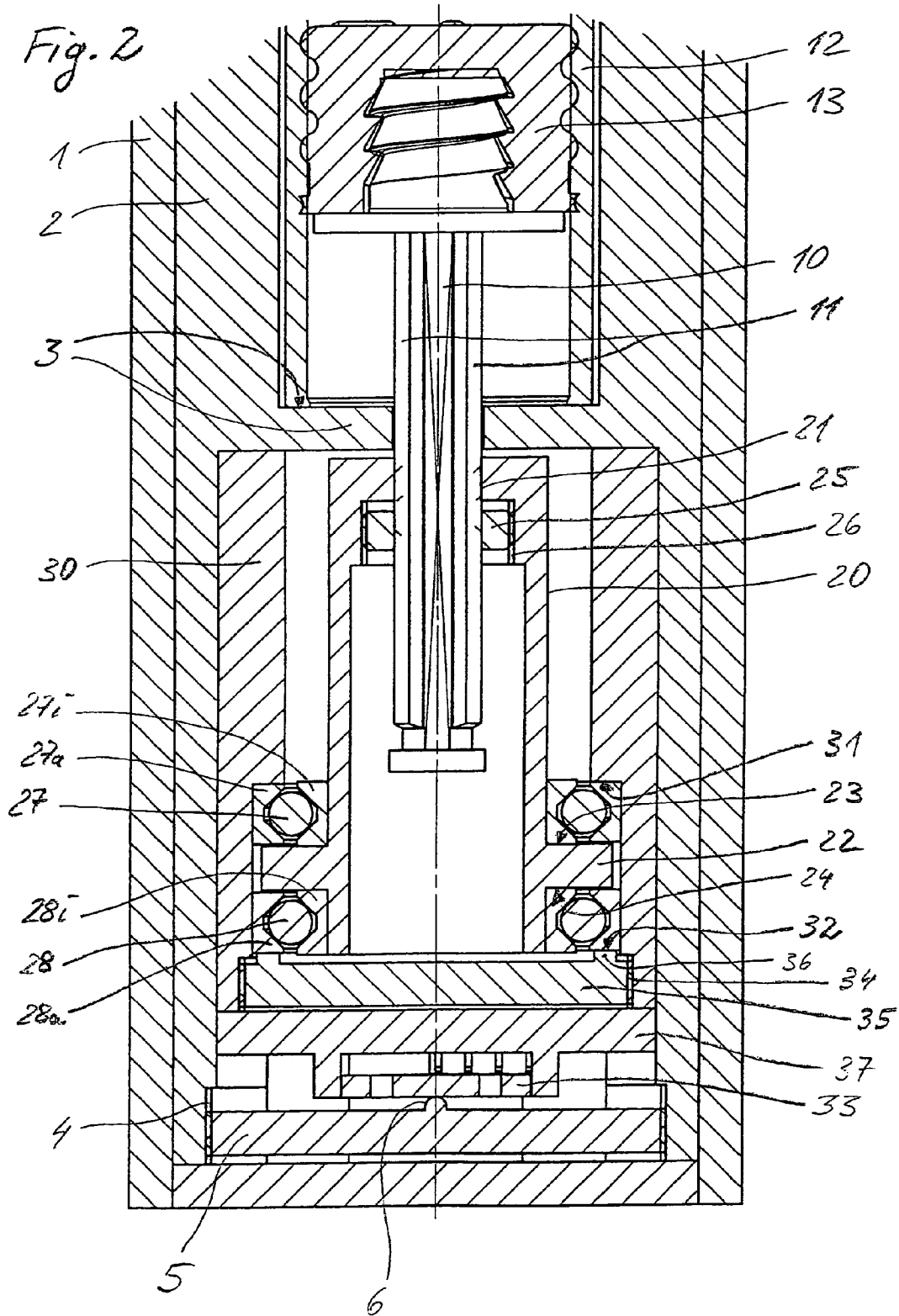
FIG. 2 shows part of the administering device of FIG. 1 in another longitudinal section.
Figure 3:
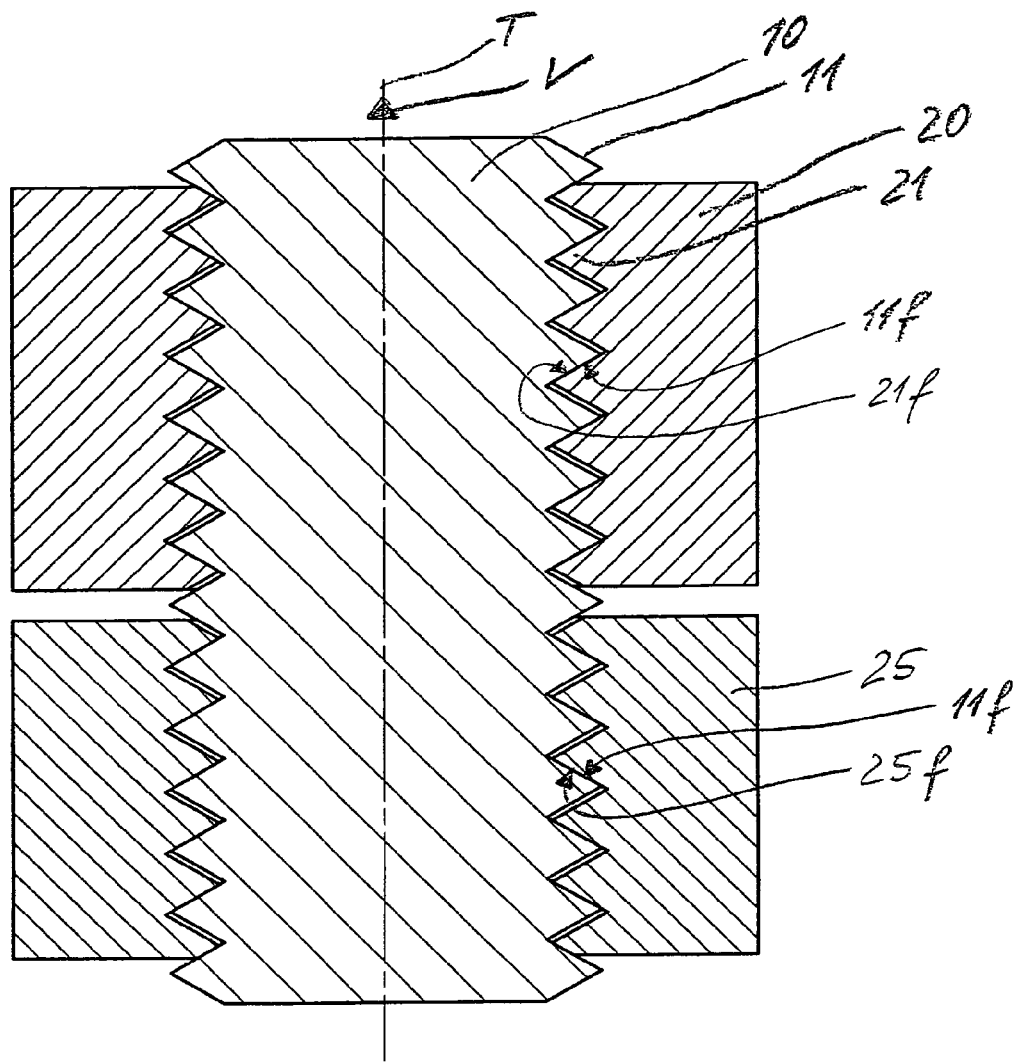
FIG. 3 shows an enlarged detail from FIG. 2.

The structure and action of the device for reducing play can be seen from FIGS. 2 and 3. The device for reducing play is formed by a one-piece adjustment member 25. The adjustment member 25 is in an adjustment engagement with the output member 10 and in a further adjustment engagement with the drive member 20. The adjustment member 25 and the two adjustment engagements are configured such that the axial play between the threads 11 and 21 is significantly reduced or eliminated.

In the illustrative embodiment, the adjustment member 25 is formed as a threaded nut with an inner thread and an outer thread. With its inner thread, the adjustment member 25 is in a threaded engagement with the outer thread 11 of the output member 10. With its outer thread, it is in a threaded engagement with an inner thread 26 of the drive member 20. The inner thread 26 is directed towards the outer thread 11 and formed axially immediately behind the thread 21. The inner thread and the outer thread of the adjustment member 25 lie at the same axial height, such that the adjustment member 25 can be axially thin and the device for reducing play can accordingly be made axially short, i.e., short along the translation axis T. The inner thread 26 may be sufficiently long that a secure adjustment engagement with the adjustment member 25 is ensured and the adjustment member 25 can additionally be displaced in this adjustment engagement such that the desired reduction of the axial play of the threads 11 and 21 can be provided. The inner thread 26 has a pitch allowing the adjustment member 25 to be displaced in threaded engagement with the inner thread 26 when threaded engagement exists between the threads 11 and 21 and between the thread 11 and the inner thread of the adjustment member 25.

FIG. 3 shows an enlarged representation of the threaded engagement of the threads 11 and 21 and the adjustment engagement between the thread 11 of the output member 10 and the inner thread of the adjustment member 25. The inner thread of the adjustment member 25 has the same pitch as the outer thread 11. In some embodiments, the pitch of the outer thread of the adjustment member 25 and of the inner thread 26 is preferably greater or smaller than the pitch of the threads 11 and 21, but so slight that the displacement of the adjustment member 25 in the adjustment engagement is possible.

For the reduction of axial play, the adjustment member 25 in its adjustment engagement with the output member 10 is set in such a way that its rear thread flanks $25f$ in relation to the delivery direction V are in contact with the front thread flanks $11f$ of the outer thread 11, while at the same time the front flanks $21f$ of the driving thread 21 are in contact with the rear flanks $11f$ of the thread 11 of the output member 10. For this purpose, the adjustment member 25 in its adjustment engagement with the drive member 20 is displaced relative to the drive member 20 counter to the delivery direction V until this state of flank contact is established. In this state, the adjustment member 25 is fixed on the drive member 20 and thereby secured. In an illustrative embodiment, the securing is produced adhesively by an adhesive agent being introduced into the adjustment engagement of the adjustment member 25 with the drive member 20. Other possibilities of cohesive connection between the adjustment member 25 and the drive member 20 are also conceivable, for example, sonic or laser welding in the adjustment position. If the inner thread 26, as in preferred embodiments, has a pitch different than the threads 11 and 21, the axial securing can be achieved by this alone or in combination with a cohesive connection. The adjustment position should be chosen such that the reduction in play causes no pressing forces, or at any rate no practically relevant pressing forces, to be exerted on the output member 10. The adjustment position is therefore chosen such that, in the threaded engagement of the threads 11 and 21, a very slight residual play remains, but one which is less or much smaller than the thread play inherent to this engagement alone, i.e. without reduced play.

In an illustrative embodiment, the adjustment position of the adjustment member 25 is chosen such that the thread 21 remains the driving thread of the drive member 20. The adjustment position could also be chosen, however, such that during adjustment the adjustment member 25 is moved against the rear thread flanks of the thread 11 and in this case the adjustment member 25 assumes the forward drive of the output member 10. Preference is given, however, to the adjustment position of the adjustment member 25 chosen for the illustrative embodiment and shown in FIG. 3.

An alternative illustrative embodiment of a device for reducing play can be seen in FIGS. 4 and 5. Compared to the components of the illustrative embodiment in FIGS. 1 to 3, only the drive member 20 and the adjustment member, identified by 15 in the alternative illustrative embodiment, are modified, whereas the other components, in particular the output member 10, are unchanged. A further difference is that the alternative device for reducing play additionally comprises an elastic restoring element 17 in the form of a mechanical compression spring.

The adjustment member 15, like the adjustment member 25 before, is inserted into the sleeve forming the drive member 20. However, the adjustment member 15 is connected to the drive member 20 such that it is displaceable in an axially linear movement and is secured against twisting. The adjustment engagement of the adjustment member 15 with the drive member 20 therefore comprises a linear guide. The linear guide is formed by an axial, straight guide track 29 on the circumferential inner surface of the output member and by an engagement member 16 (FIG. 5) of the adjustment member 15 engaging in the guide track 29. The guide track 29 is limited in the delivery direction V by the radially inwardly projecting web of the drive member 20 that forms the driving thread 21. At the rear, the guide track 29 is open so that the adjustment member 15 can be pushed in. The restoring element 17 is also fitted beforehand. The restoring element 17 is supported in the delivery direction on the web of the drive member 20 forming the driving thread 21 and is supported counter to the delivery direction on the adjustment member 15. FIG. 4 shows this state before assembly with the output member 10.

For assembly, the adjustment member 15 is first inserted with the restoring element 17 into the drive member 20 into adjustment engagement with the guide track 29 and is pressed with a certain force against the restoring element 17. The output member 10 is then initially screwed onto the adjustment member 15 and then onto the driving thread 21. In the adjustment engagement, the rear thread flanks of the inner thread of the adjustment member 15 press with an elasticity force against those thread flanks of the thread 11 of the output member 10 that point in the delivery direction V. As a result, for the threaded engagement of the threads 11 and 21 via the two adjustment engagements of the adjustment member 15, the same state is obtained as is shown in FIG. 3. In the alternative device for reducing play, the adjustment member 15 is thus secured in the adjustment position by the elasticity force of the restoring element 17.

The infusion appliance in the illustrative embodiment has as a particular feature, but one known in principle from DE 198 40 992 A, an occlusion detection mechanism, which is also inherently subject to axial play, thus detracting from the metering accuracy. This inherent second axial play has its cause in the fact that the entire delivery means, in particular the output member 10 and the drive member 20, is supported axially on the support body 2 via a sensor 33. The sensor 33 is used to determine the force necessary for moving the piston 13 along the translation axis T. The sensor can, for example, be based on strain measurement. The sensor 33 is used to measure a physical parameter representing the liquid pressure in the container 12, in order to detect any occlusion or any leakage as early as possible during the administration of the product. As regards the occlusion detection and/or leakage detection and the sensor 33, the following deals only with those aspects concerning the axial play, and in other respects reference is made by way of example to DE 198 40 992 A.

For the occlusion detection and/or leakage detection function and/or mechanism, the delivery means, as has already been mentioned, is axially supported via the sensor 33. This means that the drive member 20, on which the output member 10 is axially supported in the driving engagement of the threads 11 and 21, is not connected in an axially rigid manner to the support body 2, but is instead mounted so as to be able to move axially relative to the support body 2, to be able to determine the liquid pressure in the container 12, or more precisely the differential pressure with respect to the environment. To obtain the axially movable bearing, the drive member 20 is mounted rotatably in a bearing body 30 and is axially secured on the bearing body 30. The bearing body 30 is inserted into the second receiving space of the support body 2 and secured against twisting. The support body 2 guides the bearing body 30 axially through sliding contact. The bearing body 30, and together with it the output member 10 and drive member 20, is supported axially on the support body 2 via the sensor 33 such that the sensor 33 picks up all the axial force acting between the bearing body 30 and the support body 2 and directed counter to the delivery direction V. In the delivery direction V, the bearing body 30 abuts against the support body 2. The bearing body 30 also supports the motor 18 and the gear 19 of the delivery means. In the illustrative embodiment, it is for this purpose provided with a lateral extension piece which projects through a lateral aperture of the support body 2 into the lateral receiving space of the housing shell structure 1, which lateral receiving space accommodates the motor 18, a control means and, if appropriate, a further appliance management system. For this purpose, the jacket of the substantially hollow-cylindrical support body 2 is provided with an aperture through which the sensor 33 also protrudes with a sensor attachment face at which it is connected to the control means and to a display.

The sensor 33 forms an elastic boom which is clamped firmly at both ends. The holder for the sensor 33 serves as an integrally formed sensor carrier 37 which is guided with axial sliding by the support body 2 and abuts, via a contact point 6 and the sensor 33, against the rear edge of the aperture of the bearing body 30 or if appropriate is fixedly connected to the bearing body 30. Since the sensor carrier 37 then also participates in each axial movement of the bearing body 30, if only abutment contact exists, it is attributed to the bearing body 30 and thus to the delivery means.

To substantially eliminate the axial play between the support body 2 and the bearing body 30, or at least to reduce it to an extent that can be tolerated in respect of the metering accuracy or that is no longer detectable in practice, a contact adjustment or compensation element 5 is provided which serves as an adjustment member 5. The adjustment member 5 forms the contact point 6 for the sensor 33. The contact point 6 comprises a cam which protrudes on the translation axis T from the front face of the adjustment member 5 in delivery direction V. The bearing body 30 is axially supported via the sensor 33 only in a quasi-punctiform manner at the contact point 6 on the translation axis T.

The adjustment member 5 is in an adjustment engagement with the support body 2. In the illustrative embodiment, this adjustment engagement is also a threaded engagement, namely between an inner thread 4 at the rear end of the support body 2 and a corresponding outer thread of the adjustment member 5. The adjustment member 5 is a circular cylindrical disc whose axial thickness is selected substantially exactly such that it is provided on its outer circumference with a sufficiently long threading for sufficiently secure adjustment engagement.

The adjustment position of the adjustment member 5 is chosen such that the bearing body 30 is in abutment against the support body 2 in the delivery direction, and at the same time the contact point 6 touches the rear face of the force sensor 33. The inner thread 4 of the support body 2 is sufficiently long to screw the adjustment body 5 in and to be able to adjust it in the adjustment engagement as far as this adjustment position. The adjustment position may preferably be chosen such that a calibration curve of the calibrated sensor 33 is not changed, in particular in such a way that the zero point of the calibration curve remains constant. The offset of the sensor 33 is therefore in other words "zero" when the pressure of the liquid in the container 12 corresponds to the ambient pressure. An offset is obtained upon priming of the infusion appliance. In principle, however, the adjustment position can also be chosen such that an offset is already obtained in the adjustment position before priming. This adjustment offset should be smaller than the offset obtained upon priming. The term "priming" designates the procedure by which the product-conveying parts, including an outlet point of the catheter 8 that can be formed by an insert cannula or a soft cannula, are filled completely with the product.

In its adjustment position, the adjustment member 5 is secured on the support body 2, in some preferred embodiments, cohesively connected to the support body 2. The cohesive connection can be obtained for example by laser welding or, in some preferred embodiments, by an adhesive agent introduced into the adjustment engagement.

Even without occlusion detection and/or leakage detection, an axial play is inherent not only to the threaded engagement between the output member 10 and the drive member 20, but also to the rotary bearings, such as are known from conventional infusion appliances.

To reduce the axial play in the rotary bearing of the drive member 20, adjustment or compensation is provided by an adjustment member 35. The adjustment member 35 is in an adjustment engagement with the bearing body 30. This adjustment engagement is also a threaded engagement. Like the adjustment member 5, the adjustment member 35 is also a flat, disc-shaped screw with an outer thread. At the rear end of the bearing body 30, the adjustment member 35 is screwed into the bearing body 30, which for this purpose forms an inner thread 34 in adjustment engagement with the outer thread of the adjustment body 35. The adjustment member 35 is arranged in such a way that, beyond the forces arising from the rotary bearing, no other external forces may act on the adjustment member 35.

For the axial supporting and securing of the drive member 20, the bearing body 30 forms a first support surface 31 oriented counter to the delivery direction V, and the adjustment member 35 forms a second support surface 32 facing towards the support surface 31. The drive member 20 forms, on its web 22, a third support surface 23 which is oriented in the delivery direction V and faces towards the first support surface 31, and a fourth support surface 24 which is oriented counter to the delivery direction V and faces towards the second support surface 32. A ball bearing 27 is held axially between the two support surfaces 31 and 23, and a further ball bearing 28 is held axially between the support surfaces 32 and 24. Each of the ball bearings 27 and 28 forms a radial bearing and, via the support surfaces 31 and 23 and also 32 and 24, an axial bearing. The ball bearings have, in the customary manner, an inner bearing ring and an outer bearing ring which are able to rotate relative to one another about the translation axis T and between which in each case a plurality of balls are arranged which transmit the radial and axial forces between the bearing rings. In the ball bearing 27, the inner bearing ring is indicated by 27$i$ and the outer bearing ring by 27$a$. The ball bearing 28 correspondingly has an inner bearing ring 28$i$ and an outer bearing ring 28$a$. The inner bearing rings 27$i$ and 28$i$ are radially supported on the outer circumferential surface of the drive member 20, and the outer bearing rings 27$a$ and 28$a$ are radially supported on the opposite inner jacket surface of the bearing body 30.

For the axial clamping of the ball bearings 27 and 28, the adjustment member 35, in its adjustment position, is pressed with a slight axial force against the outer bearing ring 28$a$. The adjustment member 35 and the ball bearing 28 are in contact only with the outer bearing ring 28$a$ and the second support surface 32. The second support surface 32 is a circumferentially closed annular end face of an annular web 36 concentric to the rotation axis T, which annular web 36 protrudes in the delivery direction V from the front face of the adjustment member 35. The annular end face could also have interruptions. Similarly, the support surface 32 could be formed by individually protruding cams.

The outer bearing rings 27$a$ and 28$a$ have axially no contact with the support surfaces 23 and 24 of the drive member 20. The inner bearing rings 27$i$ and 28$i$ have axially no contact with the support surfaces 31 and 32. The axial force flow through the rotary bearing therefore runs exclusively via the contact of the support surfaces 31 and 32 with the respectively facing outer bearing ring 27$a$, 28$a$ and the contact between the support surfaces 23 and 24 and the respectively facing inner bearing ring 27$i$, 28$i$. The axial force within the ball bearings 27 and 28 is therefore transmitted substantially exclusively by the balls. In this way, apart from manufacturing tolerances of the ball bearings 27 and 28, a rotary bearing is obtained which is virtually and/or practically free of play in the axial sense.

The adjustment member 35 is secured in its adjustment position like the adjustment members already described. The securing on the bearing body 30 is likewise preferably a cohesive connection and can in particular be effected by an adhesive agent which is introduced into the adjustment engagement. However, other cohesive connections, for example sonic or laser welding, or other suitable methods or structures, are also possible. As with the other adjustment members, the securing is effected in the adjustment engagement itself.

As regards the adjustment engagements, it should also be noted that the axial lengths of the paths of displacement of the adjustment members 5, 15, 25 and 35 in the adjustment engagements are each of such length that the respective adjustment member, when displaced into the adjustment position, cannot come into abutment contact against the body with which it is in the adjustment engagement, which blocks further displacement in the same direction.

In conventional infusion appliances and also in conventional injection appliances, a further source of axial play that detracts from metering accuracy is the large difference between the axial thermal expansion of the housings and the axial thermal expansion of the reservoir containers used. The housings are normally produced from plastic by injection moulding, while the containers are in most cases glass bodies. The coefficients of thermal expansion of these materials generally differ approximately by a factor of 10, i.e., a whole order of magnitude. For axial compensation of these differences in thermal expansion, the containers in the conventional appliances are supported on the housings with elastic resilience in the axial sense. In the temperature range in which the appliances are used, which range at least covers temperatures from −20° C. to 40° C., the positions between the delivery means and the containers therefore change axially to an extent that has an appreciable effect on the metering accuracy.

This axial play, and its negative impact on metering accuracy, is countered by the support body 2 having, in the axial direction, a thermal expansion factor or capability, inherently or otherwise provided, which is much closer to the axial thermal expansion of the container 12 than is the case with the housings of conventional appliances. Thus, the support body 2 can be made from a material whose coefficient of thermal expansion differs by a factor of approximately 5 from the coefficient of thermal expansion of the material of the container 12. It is more preferable if the coefficients of thermal expansion are as close as possible to one another or even identical. Structural measures are also conceivable, for example manufacturing the support body 2 as a composite body which includes several materials within the composite, for example stiffening bodies that are embedded in plastic and that obstruct the thermal expansion of the plastic material in the axial direction. Preferred materials for obtaining favourable thermal expansion have a coefficient of thermal expansion of $30 \times 10^{-6}$/K or less in the temperature range in which they are used. The materials preferably have a thermal expansion that is uniform in all directions. However, a support structure in the form of a composite body will by nature have an irregular thermal expansion, relative to the whole composite body, so that in such a case only the axial thermal expansion and the coefficient of axial thermal expansion are meant.

Some of the preferred materials for constructing infusion appliances and injection appliances are listed in the following table, together with their coefficients of thermal expansion $\alpha$ in the temperature range within which they are used:

| Material | Coefficient of thermal expansion $\alpha$ in $10^{-6}$/K |
| --- | --- |
| Brass | 18 to 19 |
| Steel | 10 to 12 |
| Aluminium | 23 to 24 |
| Polyamide PA | 100 to 140 |
| Polyoxymethylene POM | 110 to 130 |
| Polyethyleneterephthalate PET | 70 |
| Polycarbonate PC | 70 |
| Polytetrafluoroethylene PTFE | 60 to 200 |

-continued

| Material | Coefficient of thermal expansion α in $10^{-6}$/K |
|---|---|
| Acrylonitrile/butadiene/styrene ABS | 80 to 110 |
| Glass | 5 to 10 |
| Hard rubber | 75 to 100 |

By means of a support body 2 or, more generally, a support structure 2 made, for example, of aluminium or an aluminium-based alloy, it is already possible to achieve a considerable improvement over those plastic materials which in terms of thermal expansion come closest to the container material, preferably glass, because the coefficient of thermal expansion of aluminium is smaller, approximately by a factor of 3, than the coefficient of thermal expansion of the plastic materials that come closest to the container material in terms of the coefficient of thermal expansion. A further improvement can be achieved by using a brass material. If the support structure is made of steel, or if it has steel components arranged in such a way that the axial thermal expansion is critically influenced by the steel components, it is even possible, in the most favourable case, to achieve an identical thermal expansion, with appropriate choice of the glass material. If the support body 2 or more generally a support structure 2, which of course also assumes an axial support function like the support body 2, is formed as a composite body, then stiffening bodies, for example axial fibres incorporated into a plastic matrix, can provide a comparably favourable thermal expansion behaviour, if the stiffening body or bodies have a thermal expansion as described above.

The multi-part design of the housing, in the illustrative embodiment the two-part design, can in principle even be dispensed with if the housing shell, in the illustrative embodiment the shell structure 1, has a thermal expansion according to the invention. In such a design of a housing shell, it is preferable if the housing shell is formed as a composite body, for example as a plastic matrix with embedded stiffening bodies, such as, in particular, axially oriented metal fibres or other suitable material.

Even though a support structure is already advantageous which only supports the container axially, it is more advantageous if such a support structure extends over the greatest possible length measured in the delivery direction V of the piston 13. The support structure, for example as the support body 2, should additionally provide axial support for the delivery means in both directions, too. It is also particularly expedient if the delivery means as a whole also has an axial thermal expansion as close as possible to the axial thermal expansion of the support structure, for example by the support structure and the components of the delivery means being made from the same material or, if appropriate, from different materials that have axial thermal expansions as close as possible to one another. Advantageously, the output member 10 or the drive member 20 has, or preferably both of these components have, substantially the same axial thermal expansion as the support body 2, i.e., a thermal expansion which differs at most by a factor of approximately 5 and preferably by less than a factor of 5, preferably by at most a factor of 2 or even less, from the axial thermal expansion of the support body 2 and which is ideally identical.

The greater the axial length spanned by a one-part support structure or jointly by the several support bodies of a multi-part support structure, the smaller is the axial play attributable to different axial thermal expansions. Plastic parts of conventional type have to span very short axial lengths in this case. The shorter the axial lengths spanned by conventional plastic parts, the smaller is the axial play attributable to different thermal expansions. It is particularly expedient, as in illustrative embodiments of the present invention, if such a support body, or if appropriate several support bodies arranged axially in succession, is or are provided whose axial thermal expansion is close to that of the container and/or of the delivery means. The supporting means of the support body which secure the container and/or the delivery means axially on the support body or on the support bodies should be formed in one piece by the respective support body or be connected to the respective support body in such a way that they are not axially movable relative to the support body, such as, for example, by the pair of webs 3 and 7a, the pair comprising support web 3 and adjustment member 5, and the pair comprising adjustment member 35 and support surface 31.

The support body 2 is a comparatively simple sleeve body which is inserted into the shell structure 1 and is provided for the bearing of the mutually axially movable parts and thus for axial stiffening. The shell structure 1 itself can be produced in the customary manner from plastic by injection moulding. The shell structure 1 comprises two parts, namely a top part and a base part. The top part forms the receiving chamber for the support structure 2 and for those components of the administering device that are optionally not supported by the support structure 2. The base part is a simple plate which is connected fixedly to the rear face of the top part and there closes the receiving chamber.

In some embodiments, the lid 7 is preferably made from the same material as the support body 2. This also applies to the bearing body 30, the two adjustment members 35 and 5, and the carrier disc 37, resulting overall in a support structure that is very homogeneous in respect of the axial thermal expansion. The lid 7 and/or the carrier disc 37 and/or the adjustment member 35 and/or the adjustment member 5 may be produced from one of the customary plastic materials.

Figure 6:
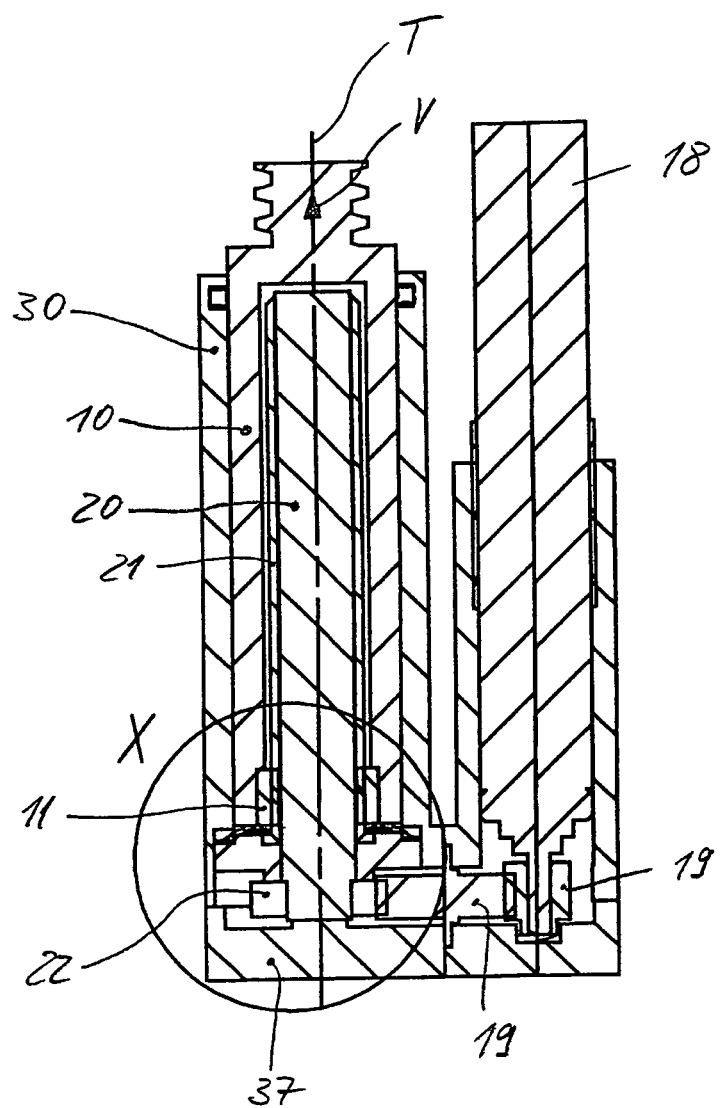
FIG. 6 is a longitudinal section through an administering device in another illustrative embodiment of the present invention.

FIG. 6 shows, in a longitudinal section, a bearing body 30 mounted in the same way as in the first illustrative embodiment, together with the components of an administering device that are supported by it, in accordance with a second illustrative embodiment, which is an infusion appliance. Those components of the second illustrative embodiment whose function and partly also whose construction are comparable with the components of the first illustrative embodiment have been given the same reference labels as in the first illustrative embodiment. Differences exist only in so far as are indicated below or as appear from the figures themselves. The statements concerning the first illustrative embodiment are intended also to apply to the embodiment of FIG. 6, unless anything is stated to the contrary.

The administering device in the second illustrative embodiment has a device for reducing play intended for eliminating or at least reducing the axial play between the rotation member 20 and the bearing body 30. In contrast to the first illustrative embodiment, the device for reducing play axially clamps the rotation member 20 directly against the sensor carrier 37. Moreover, in the second illustrative embodiment, the translation member 10 substantially surrounds the rotation member 20. The translation member 10 and the rotation member 20 are in threaded engagement with one another. For this purpose, the rotation member 20 is provided over most of its axial length with an outer thread 21, and the translation member 10 is provided with an inner thread 11 only at its rear end in relation to the direction of translation V. The translation member 10 is guided in an axially linear manner on the bearing body 30. As in the first illustrative embodiment, a motor 18, preferably an electric stepper motor, drives the rotation member 20 in a rotary movement about the rotation and translation axis T via a cylindrical gear with two toothed wheels 19 in radial engagement. For its drive, the rotation member 20 is again provided at its rear end with an outwardly toothed annular web 22 which is in radial engagement with the intermediate wheel 19 of the cylindrical gear for the rotary drive of the rotation member 20.

Figure 7:
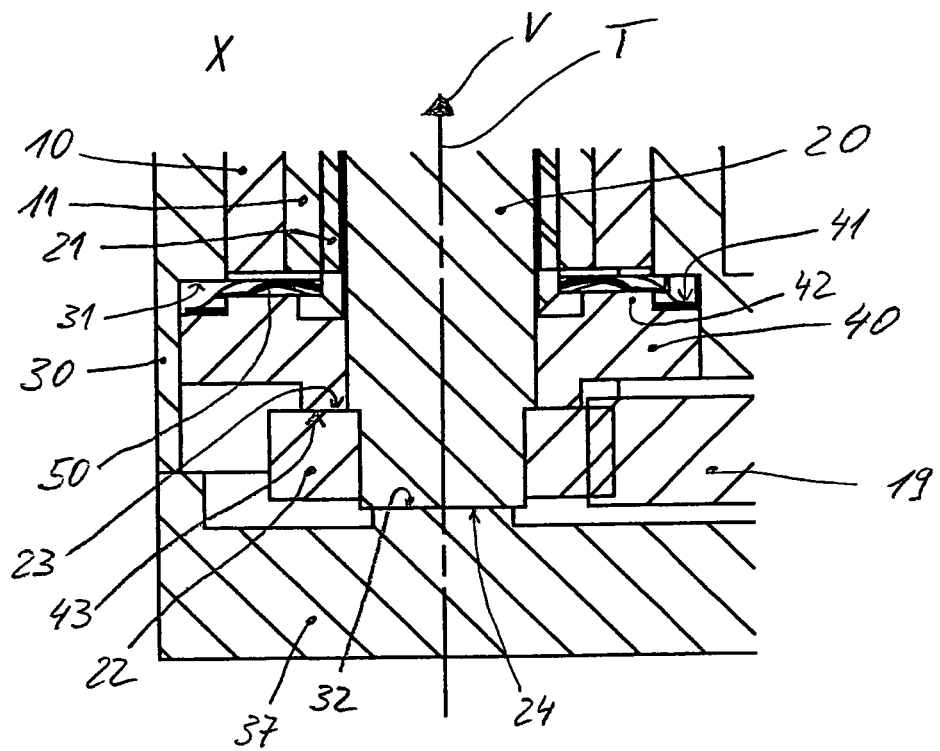
FIG. 7 shows a detail "X" from FIG. 6.

The rotary bearing of the rotation member 20 is shown in an enlarged view in FIG. 7. The rotary bearing in the second illustrative embodiment is formed as a simple slide bearing. The second support surface 32 of the sensor carrier 37 and the fourth support surface 24 of the rotation member 20 form a first slide pair surface of the rotary bearing. The two support surfaces 32 and 24 are in direct sliding contact with one another. The second support surface 32 is formed at the rear end of the rotation member 20. Protruding toward it from the sensor carrier 37, there is a short pedestal whose front face forms the second support surface 24. The pedestal frees the rotation member 20 from the sensor carrier 37. The formation of a pedestal permits more precise production of the second support surface 32. The third support surface 23 is formed in the manner of the support surface 23 in the first illustrative embodiment, namely by the front face of the annular web 22 that points in the translation direction T. The first support surface 31, facing axially towards it, is formed by the bearing body 30. However, the support surfaces 31 and 23 are radially offset from one another, i.e., they are not exactly in axial alignment. The radial offset is spanned by a transmission body 40, in the illustrative embodiment a transmission ring, which is arranged between the support surfaces 31 and 23. The transmission body 40 forms, on a front face, a front support surface 41 which lies in axial alignment opposite the first support surface 31 and which extends around the translation axis T and the rotation member 20, and it forms, on its rear face, a rear support surface 43 which lies in axial alignment opposite the third support surface 23. The rear support surface 43 is directly in abutment contact with the third support surface 23. A clear axial spacing remains between the first support surface 31 and the front support surface 41 facing towards it. An annular spring 50 is arranged between the two support surfaces 31 and 41 and bears axially on both support surfaces 31 and 41 with an axial pretensioning force.

Figure 8:
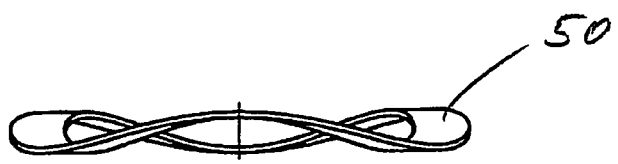
FIG. 8 shows a spring washer ring of a device for reducing play in the illustrative embodiment of FIG. 6, FIG. 9, including

The annular spring 50 is shown on its own in FIG. 8. It undulates about its perimeter and is made, for example, from spring steel. In the installed position, it bears alternately with its wave crests and wave valleys on the first support surface 31 and the front support surface 41 of the transmission body 40. Upon axial compression, it acts like a leaf spring.

As can be seen in particular from FIG. 7, the transmission body 40 not only serves to compensate for the radial offset, but also to centre the annular spring 50. For this purpose, the transmission body 40 is provided, on its front face, with an annular projection 42 about whose outer circumference the front support surface 41 extends, slightly set back axially.

The annular spring 50 and the transmission body 40 form the device or mechanism for reducing play in the second illustrative embodiment, since the transmission body 40 is axially movable relative to the bearing body 30. In some embodiments, the body is preferably guided in an axially linearly manner by the bearing body 30. In principle, however, it can move in rotation relative to the bearing body 30. Although the transmission body 40 can in principle be connected to the rotation member 20 in a manner fixed in terms of rotation, either by means of being joined thereto or by being designed in one piece with the rotation member 20, in some embodiments it is preferable if the transmission body 40, as in the illustrative embodiment, can move in rotation relative to the rotation member 20 and, even more preferably, is also axially movable. In this way, a further pair of slide surfaces of the rotary bearing is formed by the support surfaces 23 and 43 sliding directly on one another. The annular spring 50 is thus advantageously kept free from rotation movements.

In the second illustrative embodiment this provides, for the rotation member 20, an advantageously simple device for reducing play which, with sufficient pretensioning of the annular spring 50, eliminates any axial play between the rotation member 20 and the bearing body 30. In configurations in which the support surfaces 31 and 23 lie in axial alignment opposite one another, the transmission body 40 could be dispensed with. However, in order to keep the annular spring 50 free from rotation movements in these configurations too and/or to obtain an easy-to-produce centring for the annular spring 50 or also for another spring device generating the pressing force, the interposition of a transmission body in the manner of the transmission body 40 is then also of advantage.

FIG. 9, including FIGS. 9a and 9b, is an exploded view showing the bearing body 30, the rotation member 20, the transmission body 40 and the annular spring 50 in series along the imaginary translation axis, in a sequence suitable for one method of assembly in accordance with the present invention. FIG. 10 shows the translation member 10 on its own. In a first assembly step, the translation member 10 on its own can be inserted from behind into the bearing body, and the rotation member 20 can then be screwed into the translation member 10, or the threaded connection between the translation member 10 and the rotation member 20 can first be produced, and only then is the translation member 10 with the screwed-in rotation member 20 inserted into the bearing body 30. Before the rotation member 20 is screwed in, the transmission body 40 and the annular spring 50 are pushed via the outer thread 21 as far as the annular web 22 of the rotation member 20, after which the rotation member 20 is screwed into the translation member 10. After the translation member 10 and the rotation member 20 are arranged in the bearing body 30, the sensor carrier 37 is connected to the main part (shown in FIG. 9) of the bearing body 30 so that it closes the rear face of the bearing body 30 that is open for assembly purposes. The bearing body 30 and sensor carrier 37 are not movable relative to one another in the connected state. The connection is also configured such that the annular spring 50 is installed with a defined axial pretensioning force.

In the second illustrative embodiment, the threaded engagement of the threads 11 and 21 is formed as a simple threaded engagement, although, as in the first illustrative embodiment, it can also be readily formed to permit reduction of axial play by means of an additional device for reducing play.

It should also be noted that in the first illustrative embodiment a device for reducing or preferably eliminating axial play of the rotary bearing of the rotation member 20 can be formed as in the second illustrative embodiment, and that, conversely, the device for reducing play 35 based on the adjustment engagement can be provided in the second illustrative embodiment instead of the device for reducing play 40, 50. Combined forms are also conceivable. Thus, one of the roller bearings 27 and 28 could be arranged between one of the support surface pairs 31, 23 and 32, 24 or in each case one roller bearing between both support surface pairs, in which case the roller bearing or the two roller bearings would preferably each be arranged like the roller bearings 27 and 28 of the first illustrative embodiment, i.e., the annular spring 50 or an alternative spring would act only on one of the bearing shells of such a roller bearing.

Dispensing with the axially movable bearing and with the sensor 33, the bearing body 30 could be modified to form a housing with a seat for a reservoir 12 and could then serve directly as a shell structure, like the shell structure of the first illustrative embodiment. Such a shell structure can be formed like conventional housings. Alternatively, however, it can have the thermal expansion properties of the support structure 2 of the first illustrative embodiment, so that reference is made here to the explanations given in this connection with reference to the first illustrative embodiment.

Embodiments of the present invention, including preferred embodiments, have been presented for the purpose of illustration and description. They are not intended to be exhaustive or to limit the invention to the precise forms and steps disclosed. Obvious modifications or variations are possible in light of the above teachings. The embodiments were chosen and described to provide the best illustration of the principles of the invention and its practical application, and to enable one of ordinary skill in the art to utilize the invention in various embodiments and with various modifications as are suited to the particular use contemplated. All such modifications and variations are within the scope of the invention as determined by the appended claims when interpreted in accordance with the breadth they are fairly, legally, and equitably entitled.

The invention claimed is:

1. A device for metered administration of an injectable product, said device comprising:
    a) a housing having a perimeter and longitudinal axis and comprising one of a product reservoir having a width and a longitudinal axis, or a receiving seat for a product reservoir,
    b) a translation member which, to deliver the product, executes a translation movement in a translation direction,
    c) a rotation member which, for the delivery, executes a rotation movement about a rotation axis and is coupled to the translation member in such a way that it supports the translation member counter to the translation direction, and one of the movements of rotation movement and translation movement produces the other one,
    d) a rotary bearing comprising a bearing body formed by or axially supported by the housing, which bearing body bears the rotation member rotatably about the rotation axis, and which rotary bearing has a first support surface, a second support surface, a third support surface and a fourth support surface in order to secure the rotation member axially on the bearing body,
    e) the first support surface and the second support surface being connected axially rigidly to the bearing body and either facing away from one another axially or facing towards one another axially, and the third support surface facing axially towards the first support surface and the fourth support surface facing axially towards the second support surface and being axially rigidly connected to the rotation member,
    f) a device for reducing play with which at least two of the support surfaces facing axially towards one another are clamped axially to one another with a pressing force, thereby reducing an axial play of the rotary bearing; and
    g) a lid coupled to the housing that forms a connection element between a catheter and an outlet of a container for the injectable product, wherein:
        the lid has a counteracting support web to axially fix the container for the injectable product against a support shoulder,
        the container for the injectable product has a top and the top has a width,
        the lid comprises a lower portion that substantially engages a support body of the housing along the longitudinal axis of the product reservoir and an upper portion that when fully engaged extends beyond the perimeter of the housing, touching an external portion of the perimeter of the housing and extending substantially perpendicular to the longitudinal axis of the product reservoir along the perimeter of the housing and extending beyond the width of the product reservoir, such that when the lid is fully engaged the counteracting support web abuts the top of the container for the injectable product and is oriented perpendicular to the longitudinal axis of the housing, extending inwardly so as to form an opening of a smaller width than the width of the top of the container filled with injectable product, and
        the outlet of the container extends through the counteracting support web and into the catheter, wherein the entire flowpath from the container for the injectable product to the catheter is coaxial with the longitudinal axis of the product reservoir.

2. The device according to claim 1, wherein the pressing force comprises an elasticity force.

3. The device according to claim 1, wherein the device for reducing play comprises a spring for generating the pressing force.

4. The device according to claim 3, wherein the spring acts like a leaf spring.

5. The device according to claim 3, wherein the spring is an axially elastic annular body that surrounds the rotation member.

6. The device according to claim 5, wherein the annular body is undulated about its perimeter.

7. The device according to claim 1, wherein the device for reducing play comprises a transmission body axially movable relative to at least one of the housing or bearing body and arranged between two of the axially facing support surfaces for transmitting the axial pressing force between these support surfaces.

8. The device according to claim 7, wherein the transmission body is guided axially by at least one of the bearing body or housing.

9. The device according to claim 7, wherein the transmission body is guided axially by at least one of the bearing body or housing and in a manner secure against twisting.

10. The device according to claim 7, wherein the support surfaces between which the transmission body is arranged are radially offset from one another, and the transmission body spans this radial offset.

11. The device according to claim 1, wherein one of the bearing body or the housing comprises a base part, preferably a sensor carrier, having an axially protruding pedestal which, at a front face, forms the second support surface.

12. The device according to claim 11, wherein the rotation member slides in rotation on the pedestal.

13. The device according to claim 12, wherein the rotation member comprises an annular web which forms at least one of the support surfaces of the rotation member.

14. The device according to claim 1, wherein the device for reducing play forms the first or second support surface and is in an adjustment engagement with the bearing body in which the first support surface and the second support surface are displaced relative to one another into an adjustment position and are axially secured relative to one another in the adjustment position such that an axial play of the rotary bearing is reduced.

15. The device according to claim 1, wherein the device for reducing play forms the third or fourth support surface and is in an adjustment engagement with the rotation member in which the third support surface and the fourth support surface are displaced relative to one another into an adjustment position and are axially secured relative to one another in the adjustment position such that an axial play of the rotary bearing is reduced.

16. The device according to claim 1, wherein a roller bearing with a radially inner bearing ring and with a radially outer bearing ring is arranged between the first support surface and the third support surface.

17. The device according to claim 16, wherein one of the bearing rings is axially supported by the first support surface but not by the third support surface, and the other of the bearing rings is axially supported by the third support surface, but not by the first support surface.

18. The device according to claim 1, wherein a roller bearing with a radially inner bearing ring and a radially outer bearing ring is arranged between the second support surface and the fourth support surface.

19. The device according to claim 18, wherein one of the bearing rings is axially supported by the second support surface but not by the fourth support surface, and the other of the bearing rings is axially supported by the fourth support surface, but not by the second support surface.

20. The device according to claim 1, wherein the rotary bearing is a roller bearing arrangement comprising two roller bearings, wherein one of the roller bearings is arranged between the first support surface and the third support surface and the other of the roller bearings is arranged between the second support surface and the fourth support surface, the support surface of the device for reducing play being formed such that, in the adjustment engagement of the device for reducing play, it can have contact neither with the rotation member nor with the bearing body, but only with one of the roller bearings.

21. The device according to claim 20, wherein the support surface of the device for reducing play is formed such that, in the adjustment engagement of the device for reducing play, said support surface contacts just one of the bearing rings of one of the roller bearings.

22. The device according to claim 1, wherein the device for reducing play, in the adjustment position, is connected cohesively either to the bearing body or to the rotation member.

23. The device according to claim 1, wherein the device for reducing play comprises an inherently axially rigid adjustment member.

24. The device according to claim 1, wherein the rotation member forms the third support surface and the fourth support surface in one piece.

25. The device according to claim 1, wherein the device for reducing play is in adjustment engagement with the bearing body.

26. The device according to claim 25, wherein the adjustment engagement is based on a form fit and force fit.

27. The device according to claim 26, wherein the adjustment engagement is a threaded engagement.

28. The device according to claim 27, wherein the bearing body is a sleeve body surrounding the rotation member and having an inner thread in threaded engagement with an outer thread of the device for reducing play.

29. The device according to claim 1, wherein the translation member and the rotation member each form at least one engagement flank and, by the engagement flanks, are in a flank engagement such that the rotation movement of the rotation member produces the translation movement of the translation member, and wherein a further device for reducing play is provided which, in an adjustment engagement with the translation member and the rotation member, is displaced relative to the translation member and the rotation member into an adjustment position and is secured in the adjustment position such that an axial play of the flank engagement is reduced.

30. The device according to claim 29, wherein the flank engagement is a threaded engagement.

31. The device according to claim 29, wherein the adjustment engagement of the further device for reducing play with the translation member is a threaded engagement.

32. The device according to claim 29, wherein the adjustment engagement of the further device for reducing play with the rotation member is a threaded engagement.

33. The device according to claim 1, wherein a roller bearing with a radially inner bearing ring and a radially outer bearing ring is arranged between the second support surface and the fourth support surface, wherein the device for reducing play is axially arranged between the rotary member and the housing, and wherein one of the bearing rings is axially supported by the device for reducing play but not by the fourth support surface, and the other of the bearing rings is axially supported by the fourth support surface, but not by the second support surface.

34. The device according to claim 33, wherein the device for reducing play includes a web protruding axially outward therefrom in the translational direction, and wherein only one of the bearing rings is axially supported by the web.

35. The device according to claim 34, wherein the bearing body includes an inner thread in threaded engagement with an outer thread of the device for reducing play.

36. The device according to claim 1, wherein to reduce the axial play of the rotary bearing, the device for reducing play applies a force directly to a element of the device in a direction that is substantially parallel to the translation direction.

37. The device according to claim 1, wherein the pressing force is applied by the device for reducing play in the axial direction.

38. The device of claim 1 wherein the housing has a radially inwardly projecting support web forming a support shoulder for the container of the product and wherein a receiving space for the container for the product and a receiving space for the delivery means are formed.

39. The device of claim 38 wherein the lid is screwed onto the housing.

40. The device of claim 1 wherein the lid is releasably engageable.

41. The device of claim 1 wherein the catheter directly abuts the counteracting support web.

42. A device for metered administration of an injectable product, said device comprising:
  a) a housing having a perimeter and a longitudinal axis and comprising a product reservoir having a width and a longitudinal axis,
  b) a translation member which, to deliver the product, executes a translation movement in a translation direction to drive a piston accommodated in the product reservoir, wherein the product reservoir is in axial alignment with a translation axis of the translation member;
  c) a rotation member which, for the delivery, executes a rotation movement about a rotation axis and is coupled to the translation member in such a way that it supports the translation member counter to the translation direction, and one of the movements of rotation movement and translation movement produces the other one, d) a rotary bearing comprising a bearing body formed by or axially supported by the housing, which bearing body bears the rotation member rotatably about the rotation axis, and which rotary bearing has a first support surface, a second support surface, a third support surface and a fourth support surface in order to secure the rotation member axially on the bearing body, e) the first support surface and the second support surface being connected axially rigidly to the bearing body and either facing away from one another axially or facing towards one another axially, and the third support surface facing axially towards the first support surface and the fourth support surface facing axially towards the second support surface and being axially rigidly connected to the rotation member, f) a device for reducing play with which at least two of the support surfaces facing axially towards one another are clamped axially to one another with a pressing force, thereby reducing an axial play of the rotary bearing, and wherein the device for reducing play is in axial engagement with and abuts the bearing body; and g) a lid coupled to the housing comprising a counteracting support web to axially fix the position of a container for the injectable product, wherein:

the container for the injectable product has a top and the top has a width;

the lid comprises a lower portion that substantially engages a support body of the housing along the longitudinal axis of the product reservoir and an upper portion that when fully engaged extends beyond the perimeter of the housing, touching an external portion of the perimeter of the housing and extending substantially perpendicular to the longitudinal axis of the product reservoir along the perimeter of the housing and extending beyond the width of the product reservoir, such that when the lid is fully engaged the counteracting support web abuts the top of the container for the injectable product and is oriented perpendicular to the longitudinal axis of the housing, extending inwardly so as to form an opening of a smaller width than the width of the top of the container for the injectable product, and the outlet of the container extends through the counteracting support web and into the catheter, wherein the entire flowpath from the container for the injectable product to the catheter is coaxial with the longitudinal axis of the product reservoir.

43. The device of claim 42 wherein the catheter directly abuts the counteracting support web.

* * * * *

UNITED STATES PATENT AND TRADEMARK OFFICE
CERTIFICATE OF CORRECTION

PATENT NO.         : 8,529,513 B2                                                 Page 1 of 1
APPLICATION NO.    : 11/388243
DATED              : September 10, 2013
INVENTOR(S)        : Daniel Peter et al.

It is certified that error appears in the above-identified patent and that said Letters Patent is hereby corrected as shown below:

In the Specification

Col. 9, Line 64, "longitudinal of the" should read --longitudinal axis of the--.

Signed and Sealed this
Ninth Day of September, 2014

Michelle K. Lee
*Deputy Director of the United States Patent and Trademark Office*

UNITED STATES PATENT AND TRADEMARK OFFICE
CERTIFICATE OF CORRECTION

| | | |
|---|---|---|
| PATENT NO. | : 8,529,513 B2 | Page 1 of 1 |
| APPLICATION NO. | : 11/388243 | |
| DATED | : September 10, 2013 | |
| INVENTOR(S) | : Daniel Peter et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 815 days.

Signed and Sealed this
Twentieth Day of January, 2015

Michelle K. Lee
*Deputy Director of the United States Patent and Trademark Office*